US00PP08109P

United States Patent [19]

Dehan

[11] Patent Number: Plant 8,109

[45] Date of Patent: Jan. 19, 1993

[54] IMPATIENS PLANT NAMED WALTZ

[75] Inventor: Klara Dehan, Holon, Israel

[73] Assignee: Danziger - "Dan" Flower Farm, Post Beit Dagan, Israel

[21] Appl. No.: 730,607

[22] Filed: Jul. 16, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner; Foley & Lardner

[57] ABSTRACT

A new cultivar of Impatiens plant named Waltz, characterized by its compact growth habit, medium size white flower, unique flower form, small, shiny green leaves, and purple internodes.

1 Drawing Sheet

The present invention relates to a new and distinctive cultivar of New Guinea Impatiens plant, botanically known as Impatiens, and known by the cultivar name Waltz. Waltz was developed by me through controlled breeding by crossing a cultivar identified by the breeding number 121-12-A1 as the seed parent with a cultivar designated 158-11-A as the pollen parent.

Asexual reproduction by terminal or stem cuttings taken by applicant as Mishmar Hashiva, Israel has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Compact growth habit.
2. White, medium size flower.
3. The shape of the flowers is different than the shape of flowers of existing cultivars having white flower color. A first pair of petals is overlaid by a second pair of relatively narrow petals which are essentially aligned. The petals of both pairs have a single, large indentation in the outer peripheral surface. A fifth petal extends generally perpendicular to the second pair and occupies the entire area between the adjacent petal edges of the second pair of petals. The fifth petal has only a small indentation in its outer edge.
4. The leaves are shiny and dark green in color, and relatively smaller than existing New Guinea Impatiens cultivar.
5. The branches are green, with internodes purple.

The accompanying colored photographs illustrate the overall appearance of this cultivar, showing the colors as true as it is reasonably possible to obtain in a colored reproduction of this type.

The photograph at the top is a top perspective view showing a substantial area of a typical plant in bloom.

The bottom photograph is an enlarged showing of a single flower, with the unique flower form being readily visible.

The following is a detailed description of my new Impatiens cultivar based on plants produced under commercial practice in Mishmar Hashiva, Israel. The description was made in the winter and in the early spring.

Color references are made to The Royal Horticultural Society Colour Chart except where general terms of ordinary dictionary significance are used.

Parentage: 121-12-A × 158-11-A.

Propagation:

A. *Type cutting.*—Leaf cuttings with axillary buds but not flower buds.

B. *Time to initiate roots.*—8–10 days, both at 25°–30° C. summer, and 20°–22° C. in winter.

C. *Rooting habit.*—Good.

Plant description:

A. *Form.*—Compact, mounded plant.

B. *Habit of growth.*—Vigorous compact growth, with good branching.

C. *Foliage description.*—Narrow and small leaves. (1) Size: 8 cm in length and 2.5 cm in width. (2) Shape: Generally oval. (3) Texture: Shiny. (4) Margin: Finely serrated. (5) Color: Young foliage top side, between 137A and 139A; under side 137C. Mature foliage top side, between 137A and 139A; under side 137C. (6) Venation: Light green.

Flowering description:

A. *Flowering habits.*—Very floriferous, requiring 5 days from bud to flower.

B. *Natural flowering season.*—Natural flowering season is in the spring and continuous until frost. In Israel, flowering also occurs in the winter.

C. *Flower bud description.*—Normal.

D. *Flowers borne.*—5–6 buds near the top of each branch, usually two flowers open at the same time on each branch.

E. *Quantity of flowers.*—Total inflorescence at any one time is 20–30 flowers, providing a full canopy of flowers. Flowering is continuous at temperatures above approximately 10° C. and with minimum levels of light.

F. *Petals.*—(1) Shape: One pair is narrow heart shape, one pair is heart shape, and the remaining petal is separated (see photos). (2) Color: Top side when opening is 155-D, with no fading. The under side is 155-D. (3) Number of petals: Five. (4) Size of flowers: Approximately 5.5 cm in diameter.

G. *Reproductive organs.*—(1) Stamens: One in number. a. Anther color: White. b. Pollen color: White. (2) Pistils: a. Stigma: Cone shaped, green in color. b. Style: Green in color. c. Ovaries: One in number, size 1.5 mm, green in color.

I claim:

1. A new and distinct cultivar of Impatiens plant named Waltz, as illustrated and described.

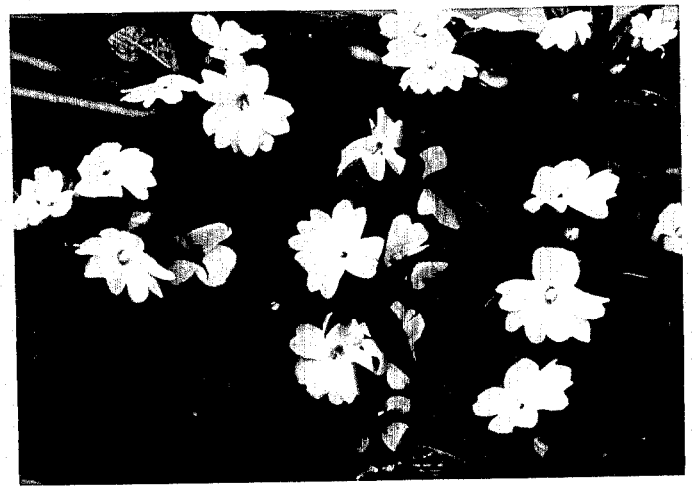
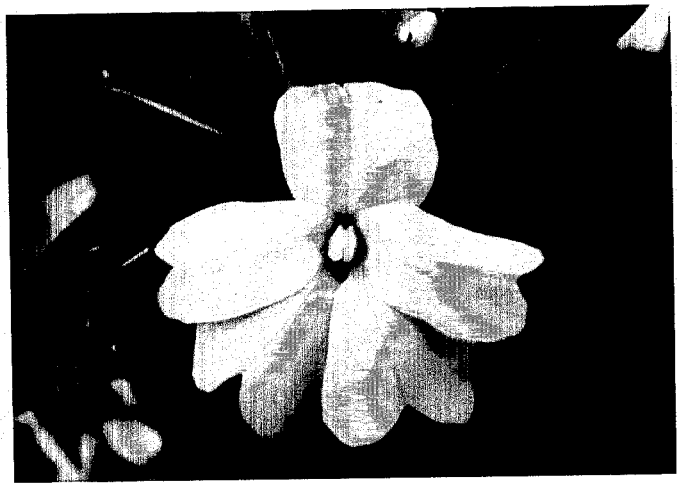

* * * * *